(12) United States Patent
Yang

(10) Patent No.: US 10,249,387 B2
(45) Date of Patent: Apr. 2, 2019

(54) METHOD FOR MANAGING AN ELECTRONIC MEDICAL RECORD AND AN EMR MANAGEMENT SYSTEM

(71) Applicant: Chien-Kang Yang, Taipei (TW)

(72) Inventor: Chien-Kang Yang, Taipei (TW)

( * ) Notice: Subject to any disclaimer, the term of this patent is extended or adjusted under 35 U.S.C. 154(b) by 532 days.

(21) Appl. No.: 14/728,222

(22) Filed: Jun. 2, 2015

(65) Prior Publication Data
US 2016/0063185 A1    Mar. 3, 2016

(30) Foreign Application Priority Data

Aug. 29, 2014 (TW) .............................. 103129932 A
Aug. 29, 2014 (TW) .............................. 103215526 U

(51) Int. Cl.
| | | |
|---|---|---|
| *G16H 10/60* | (2018.01) | |
| *G06Q 10/10* | (2012.01) | |
| *G06Q 50/24* | (2012.01) | |
| *G06F 19/00* | (2018.01) | |

(52) U.S. Cl.
CPC ............. *G16H 10/60* (2018.01); *G06F 19/00* (2013.01); *G06Q 10/10* (2013.01); *G06Q 50/24* (2013.01)

(58) Field of Classification Search
CPC ......................................... G06Q 50/22–50/24
See application file for complete search history.

(56) References Cited

U.S. PATENT DOCUMENTS

| | | |
|---|---|---|
| 2004/0168172 A1 | 8/2004 | Masuda |
| 2005/0149358 A1 | 7/2005 | Sacco |
| 2006/0047538 A1 | 3/2006 | Condurso et al. |
| 2007/0083393 A1* | 4/2007 | Howell ................. G06F 19/323 705/3 |
| 2008/0290159 A1 | 11/2008 | Bartley et al. |
| 2009/0076849 A1* | 3/2009 | Diller .................... G06F 19/323 705/3 |
| 2009/0112627 A1 | 4/2009 | Berkman et al. |

(Continued)

FOREIGN PATENT DOCUMENTS

| | | |
|---|---|---|
| TW | M306365 | 2/2007 |
| TW | 200907736 A | 2/2009 |
| TW | 201411546 A | 3/2014 |

OTHER PUBLICATIONS

Search Report for Taiwanese Patent Application No. 103129932 with English translation (2 pages).

(Continued)

*Primary Examiner* — Robert A Sorey
(74) *Attorney, Agent, or Firm* — Hamre, Schumann, Mueller & Larson, P.C.

(57) ABSTRACT

A method is for managing an electronic medical record (EMR) entry which is to be written into a data storage device possessed by a patient and includes generating information associated with a health professional who provides a health care service that results in the EMR entry, and a location which is related to the health care service, determining whether to permit writing of the EMR entry into the data storage device according to the information thus generated, determining whether the patient agrees with writing of the EMR entry into the data storage device according to input of the patient, and writing the EMR entry into the data storage device when writing of the EMR entry is permitted by the EMR management system and is agreed upon by the patient.

8 Claims, 2 Drawing Sheets

(56) References Cited

U.S. PATENT DOCUMENTS

2012/0042366 A1    2/2012  Jin
2012/0232929 A1    9/2012  Experton
2014/0081657 A1*   3/2014  Neuvonen ............. G06F 19/323
                                                              705/3

OTHER PUBLICATIONS

Search Report issued in counterpart European Patent Application No. 15177749.7 dated Feb. 19, 2016.
Search Report issued in counterpart Singapore Application No. 10201506349P dated Mar. 2, 2016.

* cited by examiner

METHOD FOR MANAGING AN ELECTRONIC MEDICAL RECORD AND AN EMR MANAGEMENT SYSTEM

CROSS-REFERENCE TO RELATED APPLICATIONS

This application claims priorities of Taiwanese Patent Applications No. 103129932 and No. 103215526, both filed on Aug. 29, 2014.

FIELD

The disclosure relates to a method and a system adapted for information management, more particularly to a method for managing an electronic medical record (EMR) and an EMR management system.

BACKGROUND

Along with the progress of information technology (IT) and the advancement of software/hardware of mobile electronic devices, IT-related applications have been developed in the health care field recently. For example, an electronic medical record (EMR) has been used by almost all levels of hospitals to replace a traditional paper medical record. Furthermore, several medical centers have published hospital application programs for download and installation in a mobile electronic device by a patient such that remote scheduling/registration can be realized by using the hospital application programs. In Taiwan, each enrollee of National Health Insurance (NHI) possesses a Health IC (Integrated Circuit) smart card. After undergoing a health care service, a medical record in a form of codes can be stored into the Health IC smart card by the hospital, such that any other medical institution is able to understand medical history of the patient in the future.

However, since the Health IC smart card is not designed for recording detailed medical records, only sixty entries of codes associated with medical records can be stored therein, which might be insufficient for a medical institution to have a good grasp of the medical conditions of the patient.

Therefore, the public and medical institutions are anxious for better circulation of EMRs. In recent years, a conventional EMR management system has been available for hospitals and clinics. The conventional EMR management system provides cloud storage spaces for allowing storage of an EMR of a patient in a cloud infrastructure by hospitals. Nevertheless, only a hospital computer that is installed with the conventional EMR management system is able to gain access to the EMR stored in the cloud storage spaces, while the patient is not able to read his/her own EMR even if he/she so wishes. Moreover, when a patient wishes for another hospital that takes over subsequent health care services to understand his/her medical history, the another hospital cannot gain access to the patient's medical records if the conventional EMR management system is not adopted. Accordingly, the present-day circulation of medical records is still unsatisfactory.

SUMMARY

Therefore, an object of the disclosure is to provide a method for managing an electronic medical record (EMR) and an EMR management system that take into account convenience, patient's privacy and circulation of medical records.

In a first aspect of the disclosure, the method is to be implemented by an EMR management system for writing the EMR into a data storage device possessed by a patient. The method includes the following steps of:

generating information associated with a health professional who provides a health care service that results in the EMR, and a location which is related to the health care service;

determining whether or not to permit writing of the EMR into the data storage device according to the information thus generated;

determining whether or not the patient agrees with writing of the EMR into the data storage device according to input of the patient; and writing the EMR into the data storage device when writing of the EMR is permitted by the EMR management system and is agreed by the patient.

In a second aspect of the disclosure, the EMR management system is configured to write an EMR into a data storage device possessed by a patient. The EMR management system includes an attendance management device, a server and a computer.

The attendance management device is configured to generate information associated with a health professional who provides a health care service that results in the EMR, and a location which is related to the health care service. The server is coupled electrically to the attendance management device for receiving the information generated thereby, and is configured to determine whether or not to permit writing of the EMR into the data storage device according to the information thus received. The computer is coupled electrically to the server, and is configured to determine whether or not the patient agrees with writing of the EMR into the data storage device according to input of the patient, and to write the EMR into the data storage device when writing of the EMR is permitted by the EMR management system and is agreed by the patient.

An effect of the disclosure resides in that a secure mechanism is utilized for writing the EMR into the data storage device possessed by the patient. It is noted that not an arbitrary individual is permitted to write or edit the EMR. After the EMR has been written into the data storage device, the EMR cannot be read and displayed unless the patient agrees. A health professional who takes over the following health care service may understand the patient's medical history with ease. In this way, an idea that the EMR is brought by the patient for achieving secure circulation of medical records may be realized.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
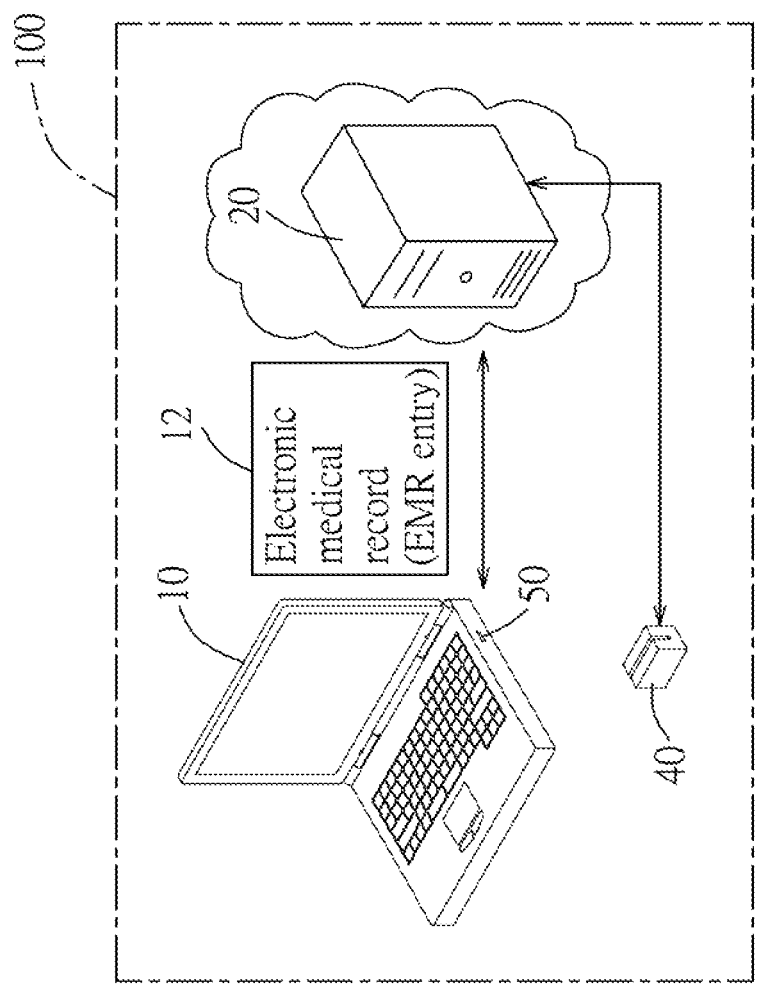
FIG. 1 is a schematic diagram illustrating an embodiment of an electronic medical record (EMR) management system according to the disclosure.
Figure 2:
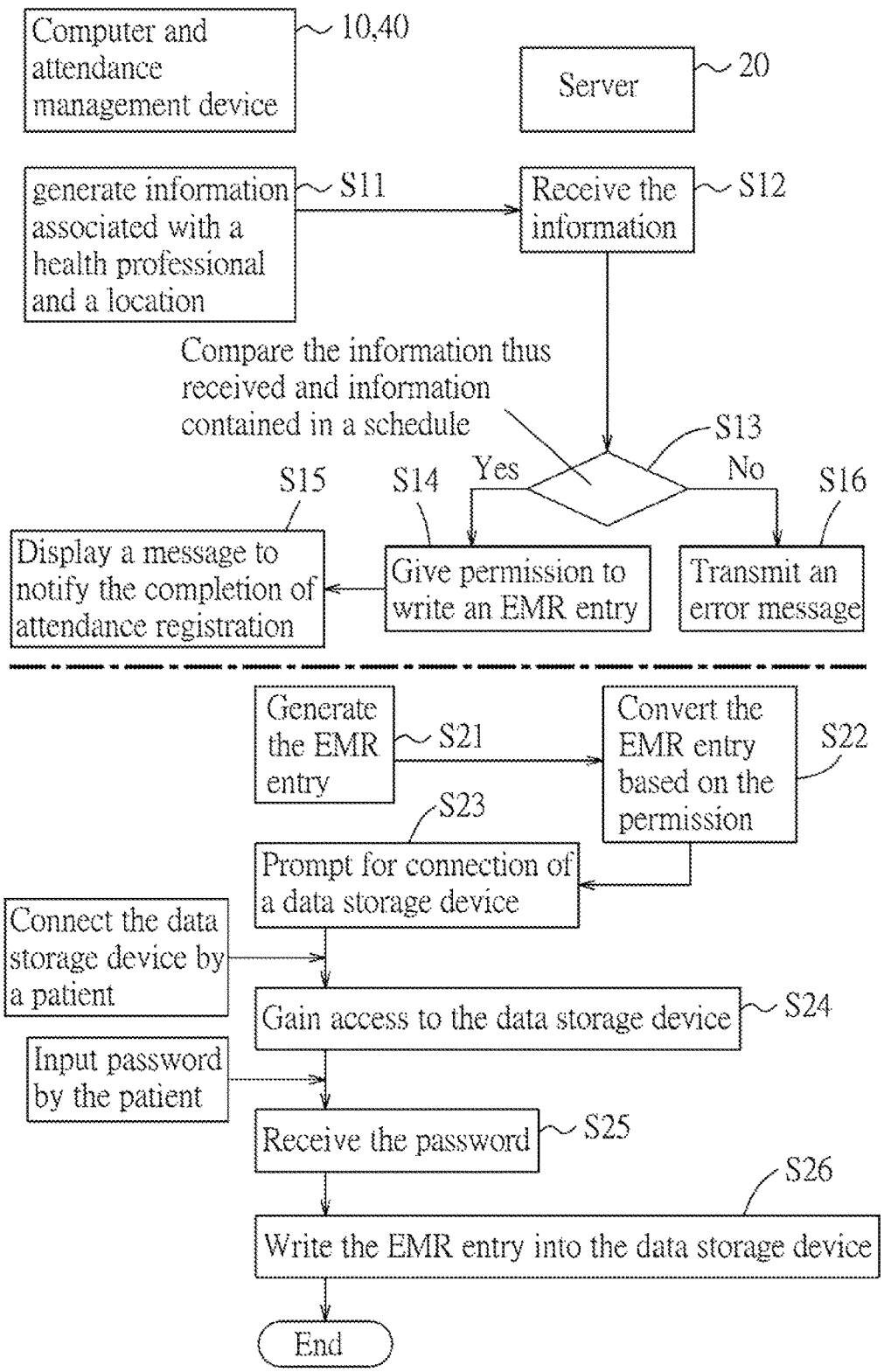
FIG. 2 is a flow chart illustrating an embodiment of a method for managing an EMR according to the disclosure.

Referring to FIG. 1 and FIG. 2, an embodiment of a method for managing an electronic medical record (EMR) according to the disclosure is to be implemented by an EMR management system 100, which is configured for writing an EMR entry 12 into a data storage device 30 possessed by a patient. In one example, the EMR management system 100 is to be set up in a medical institution with multiple examination rooms. The EMR management system 100 includes a server 20 which is to be disposed on a cloud infrastructure or at any location in the medical institution, and a plurality of computers 10 each of which is coupled to the server 20 and is to be disposed in a respective one of the examination rooms (only a single computer 10 is shown in FIG. 1). The EMR entry 12 described in this disclosure refers to any medical data. Contents of the medical data may include a result of a health care service, medication, a medical treatment, a name of an operation, a discharge summary, and so forth. The medical institution described herein refers to any level of hospitals, clinics, health centers, etc., that may generate EMR entries 12. The computer 10 refers to an electronic device which is capable of computation, and storage of data and which is disposed at a location where a health care service is performed.

In this embodiment, the EMR management system 100 further includes a plurality of attendance management devices 40 (only one is shown in FIG. 1), each of which is coupled to the server 20 and is to be disposed in proximity of a respective one of the examination rooms for recording attendance of a health professional, and is, for instance, a card reader capable of reading a staff identification (ID) card of the health professional. For example, when a doctor arrives at an appointed examination room at an arranged firms according to a schedule, and punches in using the respective attendance management device 40 with a staff ID card, attendance registration at the appointed examination room is completed.

Accordingly, referring to FIG. 2, in step S11, the attendance management device 40 is configured to generate information associated with the health professional who provides a health care service and the location which relates to the health care service (e.g., a particular examination room). In another example, the health professional may complete attendance registration through a punch-in software program by operating an electronic device that relates to said location, such as the computer 10 in the particular examination room. In the following paragraphs, attendance registration of a doctor is given as an example for explanation purposes. It is noted that the EMR management system 100 is applicable to any kind of health care institutions for use by any health professional who provides health care services.

The server 20 stores in advance a schedule that contains information associated with the health professional and the location. The server 20 determines whether or not to permit writing of the EMR entry 12 into the data storage device 30 according to the information generated by the attendance management device 40.

Specifically, in step S12, the server 20 is configured to receive the information generated and transmitted by the attendance management device 40.

In step S13, the server 20 is further configured to compare the information received from the attendance management device 40 and the information contained in the schedule.

In step S14, the server 20 is further configured to give permission, to the computer 10 in the examination room, to write the EMR entry 12 into the data storage device 30 when the information received from the attendance management device 40 conforms to the information contained in the schedule. That is to say, the identity of the doctor, time and the examination room match the scheduled ones. The server 20 then transmits a message associated with completion of the attendance registration to the computer 10.

In step S15, the computer 10 is configured to display the message to notify the completion of the attendance registration. In this way, the doctor can acknowledge that he/she is permitted to write the EMR entry 12 into the data storage device 30 by operating the computer 10 in the examination room within a duration of performance of the health care service.

In step S16, when the information received from the attendance management device 40 does not conform to the information contained in the schedule, the server 20 is configured to transmit an error message to the computer 10, and the flow ends.

In this embodiment, the patient is able to use a mobile electronic device to download and install a hospital scheduling application program (APR) published cooperatively by the medical institution and a company that issues the data storage device 30. The patient may schedule a health care service and input a symptom beforehand using the hospital scheduling APP. The hospital scheduling APP further provides an option for selection by the patient of writing EMR entry into the data storage device. When the patient selects the option while scheduling the health care service, the hospital scheduling APP transmits the selection of the option in combination with other scheduling information to the medical institution. Techniques related to the hospital scheduling APP and processing of the scheduling information are currently available to be used in combination with the EMR management system 100 of this disclosure. Since the disclosure does not focus on these techniques, detailed descriptions of the same are omitted herein for the sake of brevity.

When the patient at the scheduled time arrives at the examination room where the doctor has completed the attendance registration, the computer 10 displays the scheduling information of the patient and the symptom, to be reviewed by the doctor. After the health care service has finished, the doctor may input a diagnosis, information related to medication, etc., into the computer 10.

Accordingly, in step S21, the computer 10 is configured to generate the EMR entry 12 according to health information which results from the health care service and which is inputted by the health professional who provides the health care service. The computer 10 subsequently transmits the EMR entry 12 to the server 20.

In step S22, after receiving the EMR entry 12 from the computer 10 which is given the permission to write the EMR entry 12, the server 20 is configured to convert, based on the write permission given to the computer 10, the EMR entry 12 to an Extensible Markup Language (XML)-based format to obtain an XML-based EMR entry which is to be written into the data storage device 30. The server 20 then transmits the XML-based EMR entry back to the computer 10.

In this embodiment, specifically, in step S22, the server 20 is further configured to convert the EMR entry 12 thus received to a two-dimensional barcode, such as a QR code, and to insert the two-dimensional barcode into the XML-based EMR entry for being scanned during browsing of the XML-based EMR entry.

Since the patient has selected the option of writing EMR entry into the data storage device during the process of scheduling the health care service using the hospital scheduling APP, in step S23, the computer 10 is configured to display a message to prompt the patient to connect the data storage device 30 to the computer 10. If the patient did not select the option of writing EMR entry into the data storage device 30 during the process of scheduling the health care service, the doctor may also directly ask whether the patient wishes to have the EMR entry 12 written into the data storage device 30. If the patient agrees with writing of the EMR entry 12 into the data storage device 30, the patient is then requested to connect the data storage device 30 to the computer 10.

The data storage device 30, in other words, a carrier, may include a memory card which is possessed by the patient and which can be carried by the patient with ease. The data storage device 30 is exemplified as a Secure Digital (SB) card inserted in a portable electronic device, or a memory card disposed in a portable connector device with one of a Universal Serial Bus (USB) connector and a mini-USB connector.

The EMR management system 100 further includes a read/write device 50 coupled to the computer 10. The data storage device 30 can be connected to the computer 10 in the examination room through the read/write device 50, such as an adaptor cable, a connector interface, a combination thereof or a card reader. In other words, the computer 10 is able to access the data storage device 30 through the read/write device 50.

Furthermore, the data storage device 30 includes a control chip 31 which is designed in advance to contain a storage space for storing EMR entries from medical institutions. The control chip 31 stores in advance a dedicated password corresponding to the data storage device 30, i.e., a password required for accessing the data storage device 30.

In step S24, when the patient connects the data storage device 30 to the read/write device 50 of the computer 10, the computer 10 is connected with the data storage device 30. The computer 10 in the examination room, in response, displays a message to prompt the patient to input the dedicated password corresponding to the data storage device 30.

In step S25, when the patient operates the portable electronic device into which the SD card is inserted for inputting the password, or operates the computer 10 to input the password, the computer 10 is configured to receive the password inputted by the patient. The computer 10 then transmits the password thus received to the data storage device 30 to enable the control chip 31 of the data storage device 30 to verify whether the password is valid or invalid. The computer 10 is configured to determine that the patient agrees with writing of the EMR entry 12 into the data storage device 30 upon receipt from the data storage device 30 a response that indicates validity of the password.

In step S26, the computer 10 is further configured to write the XML-based EMR entry into the data storage device 30.

After the EMR entry 12 in the XML-based format has been written into the data storage device 30, the patient may take back the data storage device 30 and have an up-to-date EMR (containing the most recent EMR entry 12 and any other previous EMR entries already stored therein) on him/her. Once the health care service in the scheduled period is completed, the doctor may punch out using the attendance management device 40 with the staff ID card, i.e., to register the departure from work. After the departure registration has completed, the server 20 is configured to withdraw the permission, from the computer 10 in the examination room, to write the EMR entry 12 into the data storage device 30.

It is noted that, each EMR entry 12 contains medical information to be read by a health professional such that corresponding measures may be taken. Therefore, if the EMR entries 12 can be stored in a medium suitable for circulation, the quality of health care services can be promoted by making the best use of the health information. On the other hand, since the EMR contains private personal data of the patient, privacy of the EMR should be considered. Therefore, the disclosure introduces processing procedures that require the aforementioned proper permission to write and access the EMR. In the future, when the patient who uses the method for managing an EMR and the EMR management system 100 of this disclosure receives a health care service in another medical institution, the EMR can be provided to said another medical institution. For example, the patient operates the portable electronic device to execute an EMR application program to read and display the EMR with one or more EMR entries 12. Alternatively, when the EMR entry 12 in the XML-based format contains the two-dimensional bar code, i.e., the QR code, a medical professional in said another medical institution may use a scanner to scan the QR code so as to read the EMR entry 12. In a further example, a card reader may be utilized to read the memory card of the data storage device 30, and an EMR entry 12 stored in the data storage device 30 can be read after the password dedicated to the data storage device 30 has been inputted and verified as valid.

In this way, the EMR entry 12 is written into the data storage device 30 possessed by the patient and is read from the data storage device 30 only under a condition that the patient agrees. The data storage device 30 is protected, by a dedicated password rather than being readable and writable by anyone, so as to ensure privacy of the patient. On the other hand, writing of the EMR entry 12 is executed by the computer 10 in the examination room which is given the permission to write the EMR entry 12 into the data storage device 30. If an appropriate doctor or an examination room is not scheduled by the medical institution, the computer 10 cannot be given the permission to write the EMR entry 12 into the data storage device 30, that is to say, any arbitrary person who uses a random computer may not implement writing ox the EMR entry 12. In this manner, credibility of the EMR entry 12 can be ensured. Moreover, according to the mechanism of the disclosure, the EMR entry 12 is circulated along with the patient, such that the health professional is able to read the EMR entry 12 with ease and to take corresponding measures so as to facilitate the health care service.

It is noted that the EMR management system 100 that implements the method for managing an EMR of the disclosure is not limited to the disclosed embodiment, and may be a single integrated apparatus that includes the computer 10, the attendance management device 40 and the server 20. Furthermore, writing of the EMR entry 12 is exemplified to take place in the examination room, according to this embodiment. However, it maybe readily known to the person skilled in the relevant art that the location where the EMR entry 12 is written into the data storage device 30 may vary, for example, to be in a payment counter of the hospital or a pharmaceutical dispensary.

To sum up, by virtue the secure mechanism of the disclosure, the EMR entry 12 may be written into the data storage device 30 possessed by the patient, such that an idea that the EMR is brought by the patient for achieving secure circulation of medical records may be realized.

While the disclosure has been described in connection with what is(are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for managing an electronic medical record (EMR), the method to be implemented by an EMR management system for writing an EMR entry into a data storage device possessed by a patient, the EMR management system including a server, an attendance management device that is coupled to the server and that is disposed in proximity of a location where a health care service is to be performed for recording attendance of a health professional, and a computer that is coupled to the server and that is disposed at the location and that is separate from the attendance management device, the EMR management system storing in advance a schedule that contains information associated with the health professional and the location, the method comprising the steps of:

generating, by the attendance management device, information associated with the health professional who provides the health care service that results in the EMR entry, and the location which is related to the health care service when the attendance management device is operated for attendance registration by the health professional;

determining, by the server, whether or not to permit writing of the EMR entry into the data storage device by comparing the information generated by the attendance management device and the information contained in the schedule;

the server giving the computer permission to write the EMR entry into the data storage device when it is determined that the information generated by the attendance management device conforms to the information contained in the schedule;

determining, by the computer when the data storage device is used to be connected to the computer, whether or not the patient agrees with writing of the EMR entry into the data storage device according to input of the patient;

writing, by the computer, the EMR entry into the data storage device when writing of the EMR entry is permitted by the server of the EMR management system and is agreed upon by the patient; and withdrawing, by the server, the permission to write the EMR entry into the data storage device when departure registration, which is made by the health professional by punching out using the attendance management device, has completed for achieving secure circulation of medical records.

2. The method of claim 1, the EMR management system further including a read/write device coupled to the computer and to be coupled to the data storage device, the data storage device including a control chip, wherein the step of determining whether or not the patient agrees with writing of the EMR includes following sub-steps to be performed by the computer which was given the permission:

accessing, via the read/write device, the data storage device;

receiving a password which is inputted by the patient and which corresponds to the data storage device;

transmitting the password thus received to the data storage device, the password enabling the control chip of the data storage device to verify whether the password is valid or invalid; and determining that the patient agrees with writing of the EMR entry when receiving from the data storage device a response that indicates validity of the password.

3. The method of claim 1, prior to writing the EMR into the data storage device, further comprising:

generating the EMR entry according to health information which results from the health care service and which is inputted by the health professional who provides the health care service; and converting the EMR entry thus received to an Extensible Markup Language (XML)-based format to obtain an XML-based EMR entry which is to be written into the data storage device.

4. The method of claim 3, wherein the step of converting the EMR entry includes:

converting the EMR entry thus received to a two-dimensional barcode, and inserting the two-dimensional barcode into the XML-based EMR entry for being scanned during browsing of the XML-based EMR entry.

5. An electronic medical record (EMR) management system configured to write an EMR entry into a data storage device possessed by a patient, the EMR management system comprising:

an attendance management device to be disposed in proximity of a location where a health care service is to be performed for recording attendance of a health professional and configured to generate information associated with the health professional who provides the health care service that results in the EMR entry, and the location which is related to the health care service when said attendance management device is operated for attendance registration by the health professional;

a server storing in advance a schedule that contains information associated with the health professional and the location, coupled electrically to said attendance management device for receiving the information generated thereby, and configured to determine whether or not to permit writing of the EMR entry into the data storage device by comparing the information received from said attendance management device and the information contained in the schedule, said server being further configured to give permission to write the EMR entry into the data storage device when it is determined that the information received from the attendance management device conforms to the information contained in the schedule; and a computer coupled electrically to said server, disposed at the location and that is separate from the attendance management device, and configured to, when given the permission, determine, when the data storage device is used to be connected to said computer, whether or not the patient agrees with writing of the EMR entry into the data storage device according to input of the patient, and write the EMR entry into the data storage device when writing of the EMR entry is permitted by the server of the EMR management system and is agreed upon by the patient, wherein said server is further configured to withdraw, from said computer which was given the permission, the permission to write the EMR entry into the data storage device when departure registration, which is made by the health professional by punching out using said attendance management device, has completed for achieving secure circulation of medical records.

6. The EMR management system of claim 5, the data storage device including a control chip, said EMR management system further comprising a read/write device to be coupled to the data storage device;

wherein said computer which was given the permission is configured to access, via said read/write device, the data storage device, receive a password which is inputted by the patient and which corresponds to the data storage device; and transmit the password thus received to the data storage device, the password enabling the control chip of the data storage device to verify whether the password is valid or invalid, and determine that the patient agrees with writing of the EMR entry upon receipt from the data storage device of a response that indicates validity of the password.

7. The EMR management system of claim 5, wherein said server is further configured to:

generate the EMR entry according to health information which results from the health care service and which is inputted by the health professional who provides the health care service; and convert the EMR entry thus received to an Extensible Markup Language (XML)-based format to obtain an XML-based EMR entry which is to be written into the data storage device.

8. The EMR management system of claim 7, wherein said server is further configured to convert the EMR entry thus received to a two-dimensional barcode, and to insert the two-dimensional barcode into the XML-based EMR entry for being scanned during browsing of the XML-based EMR entry.

\* \* \* \* \*